(12) United States Patent
Parodi

(10) Patent No.: US 6,344,054 B1
(45) Date of Patent: Feb. 5, 2002

(54) ENDOLUMINAL PROSTHESIS COMPRISING STENT AND OVERLYING GRAFT COVER, AND SYSTEM AND METHOD FOR DEPLOYMENT THEREOF

(76) Inventor: Juan Carlos Parodi, Blanco Encalada 1543/47 1 piso, Ciudad de Buenos Aires (AR)

( * ) Notice: Subject to any disclaimer, the term of this patent is extended or adjusted under 35 U.S.C. 154(b) by 0 days.

(21) Appl. No.: 09/337,306

(22) Filed: Jun. 21, 1999

Related U.S. Application Data

(63) Continuation of application No. 08/931,992, filed on Sep. 17, 1997, now Pat. No. 5,954,764.

(30) Foreign Application Priority Data

Sep. 20, 1996 (AR) ................................................ 338240

(51) Int. Cl.[7] ................................................ A61F 2/00
(52) U.S. Cl. ...................................................... 623/1.13
(58) Field of Search ............................... 623/1.13, 1.17, 623/1.23

(56) References Cited

U.S. PATENT DOCUMENTS

| | | | |
|---|---|---|---|
| 5,282,824 A | * | 2/1994 | Gianturco ................... 623/1.13 |
| 5,405,378 A | | 4/1995 | Strecker |
| 5,667,523 A | * | 9/1997 | Bynon ........................ 623/1.11 |
| 5,693,083 A | | 12/1997 | Baker et al. |
| 5,709,703 A | | 1/1998 | Lukic et al. |
| 5,723,003 A | | 3/1998 | Winston et al. |
| 5,733,267 A | | 3/1998 | Del Toro |
| 5,746,766 A | | 5/1998 | Edoga |
| 5,749,848 A | | 5/1998 | Jang et al. |
| 5,824,041 A | | 10/1998 | Lenker et al. |
| 6,143,022 A | * | 11/2000 | Shull ......................... 623/1.13 |

FOREIGN PATENT DOCUMENTS

EP 657142 A2 * 6/1995 ................ 623/1.13

* cited by examiner

Primary Examiner—Michael J. Milano
(74) Attorney, Agent, or Firm—Ratner & Prestia

(57) ABSTRACT

A prosthesis comprising a graft and an expandable stent underlying the graft, the stent and graft being linked together only at or near their distal ends. The difference in stent length between compressed and expanded radial configurations may exceed the difference in graft length between such configurations. An introducer for such prosthesis comprises an interior sheath axially mounted inside an exterior sheath, with the graft positioned between the interior and exterior sheaths and the stent compressed at least partially inside the interior sheath. A method for deploying the prosthesis using such an introducer may include positioning the introducer distal end upstream relative to proximally flowing endoluminal fluid so that the endoluminal fluid may flow between the graft and inner sheath during stent deployment.

13 Claims, 3 Drawing Sheets

ENDOLUMINAL PROSTHESIS COMPRISING STENT AND OVERLYING GRAFT COVER, AND SYSTEM AND METHOD FOR DEPLOYMENT THEREOF

This application is a continuation of prior application Ser. No. 08/931,992, filed Sep. 17, 1997, now U.S. Pat. No. 5,954,764.

FIELD OF THE INVENTION

The present invention relates generally to endoluminal prostheses, and more specifically to an endoluminal prosthesis comprising a stent with an overlying graft cover, and a delivery system and method for delivering and deploying the prosthesis.

BACKGROUND OF THE INVENTION

As an alternative to traditional surgical vascular treatments where tissues are cut to reach a damaged artery or vein, "endovascular" treatments are now frequently used. Endovascular and related treatments are carried out at the lumen of the vessel. Some exemplary purposes and means for such treatments may be:

a) to produce artery or vein dilatation,
b) to dissolve thrombus in their interior,
c) to close abnormal communications of vessels among each other or with neighboring tissues,
d) to carpet the surface of a vessel with a prosthesis, as a "sheathing",
e) to return a dilated artery (aneurysm) to its normal caliber, or
f) to isolate the inner surface of an artery from the blood chemical or physical elements, such as, for example, after performing dilatation with a balloon (internal bypass).

Endovascular expanders, commonly known as "stents", are often used to carry out the above techniques. Stents are generally tubular, permeable, elastic structures that are typically structured in special metallic meshes forming skeletal expandable tubes able to generate radial forces to keep vessels open.

Essentially, there are three general types of stents: thermosensitive self-expanding stents, which adopt predetermined shapes at different temperatures, particularly that of the human body (such as, for example, as described in U.S. Pat. No. 4,425,908); stents expandable with a balloon (such as, for example, as described in European Patent EP 378151), and stents that are self-expandable through structural elasticity (such as, for example, as described in U.S. Pat. No. 4,580,568 to Cesare Gianturco).

Self-expandable stents are typically compressed inside introductory devices or sheaths. Once the vascular area is reached, the sheath is removed, allowing the stent to expand into an endoluminal deployment location. Commonly used stents of this type are described in patents to Cesare Gianturco or in patents assigned to Schneider (USA) Inc. of Plymouth, Minn. or Schneider (Europe) A. G. of Bulach, Switzerland.

Because of their structure, self-expanding stents typically experience longitudinal lengthening when compressed inside the sheath. When liberated inside the vascular lumen, they radially expand and longitudinally reduce. This change in shape poses a serious problem when the stent is part of a prosthesis wherein the stent is covered or lined with a Dacron or a polytetraethylene graft outside of the stent.

When the stent is deployed and expansion occurs, the length of the graft remains essentially unchanged, while the stent noticeably shortens. For example, referring now to FIGS. 1 and 2, there are shown a compressed stent 12 and compressed graft 13 in FIG. 1 and an expanded stent 12' and expanded graft 13' in FIG. 2. FIGS. 1 and 2 illustrate the relatively substantial change in length of stent 12 upon expansion as compared to the insubstantial change in length of graft 13.

Thus, a graft that is the same length as the stent inside the sheath is too long when the stent is liberated. On the contrary, if the graft is too much shorter than the stent inside the sheath, parts of the stent remain without graft cover when the stent opens. Because of the different expansion properties between the graft and the stent, and the frictional relationship between the two in the sheath, irregular expansion of the graft may occur during deployment, provoking folds on the graft that act as constrictor rings to limit the expansion of the stent.

Thus there is a need in the art for a prosthesis, and a system and method for deployment thereof, that eliminates such problems associated with concurrent deployment of a stent and graft.

BRIEF SUMMARY OF THE INVENTION

The present invention provides a prosthesis adapted for deployment inside a body lumen in a distal deployment location from a proximal access location outside the body lumen. The prosthesis comprises a graft having flexible walls and a distal end, and an expandable stent underlying the graft and having a proximal end and a distal end, the stent and graft being linked together only at or near the distal ends thereof. The stent and graft may each have a compressed radial configuration and an expanded radial configuration, each configuration having a corresponding axial length. The length of the stent in its compressed configuration exceeds the length of the stent in its expanded configuration by a difference in stent length. The length of the graft in its expanded configuration may be essentially equal to the graft in its compressed configuration, or may exceed the length of the graft in its compressed configuration by a difference in graft length. In either case, the difference in stent length exceeds the difference in graft length.

The present invention also includes an introducer adapted to endoluminally deploy such a prosthesis inside a body lumen in a distal deployment location from a proximal access location outside the body lumen, the introducer comprising an exterior sheath and an interior sheath axially mounted inside the exterior sheath. The graft is positioned between the interior and exterior sheaths and the stent is compressed at least partially inside the interior sheath.

The invention also includes a method for deploying an endoluminal prosthesis in accordance with this invention. The method comprises introducing the prosthesis into a deployment location in the body lumen using an introducer according to this invention, retracting the exterior sheath to liberate the graft therefrom, and then retracting the interior sheath to enable the stent to radially expand against the graft and bias the graft against the body lumen. The method may further comprise introducing the introducer into the deployment location with the introducer distal end located upstream relative to proximally flowing endoluminal fluid within the body lumen. During deployment of the stent, endoluminal fluid may flow between the graft and the inner sheath. In particular, the method may be used for deploying a prosthesis according to the present invention in a vascular lumen, wherein blood may flow between the graft and the inner sheath during deployment of the stent.

It is to be understood that both the foregoing general description and the following detailed description are exemplary, but are not restrictive, of the invention.

BRIEF DESCRIPTION OF THE DRAWING

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures.

The same reference numbers in the Figures indicate equal or corresponding parts. It should be understood that this drawing illustrates one or more exemplary embodiments of the invention as an illustrative example, without limitation thereto.

DETAILED DESCRIPTION OF THE INVENTION

Figure 3A:
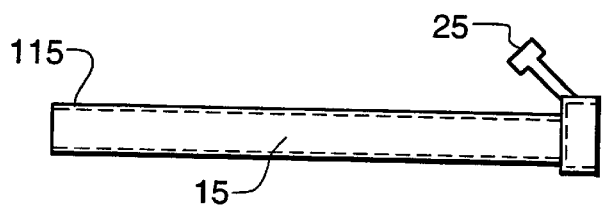
FIG. 3A is a schematic illustration of a side view of an interior sheath of an exemplary introducer of the present invention.
Figure 3B:
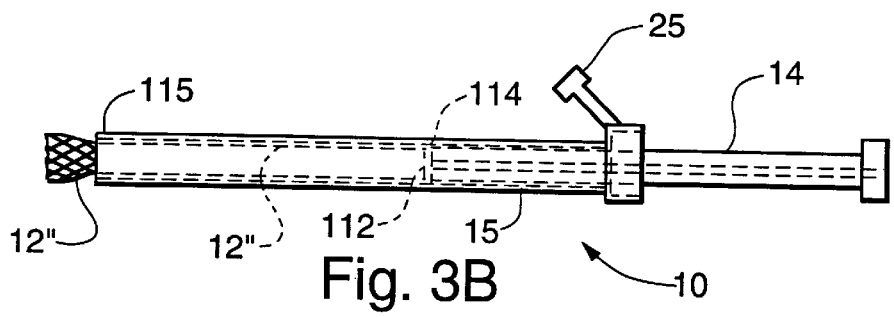
FIG. 3B is a schematic illustration of a side view of the interior sheath of FIG. 3A, showing the distal end of the sheath protruding therefrom and showing with dotted lines the interior arrangement of the pusher and the compressed stent.
Figure 3C:
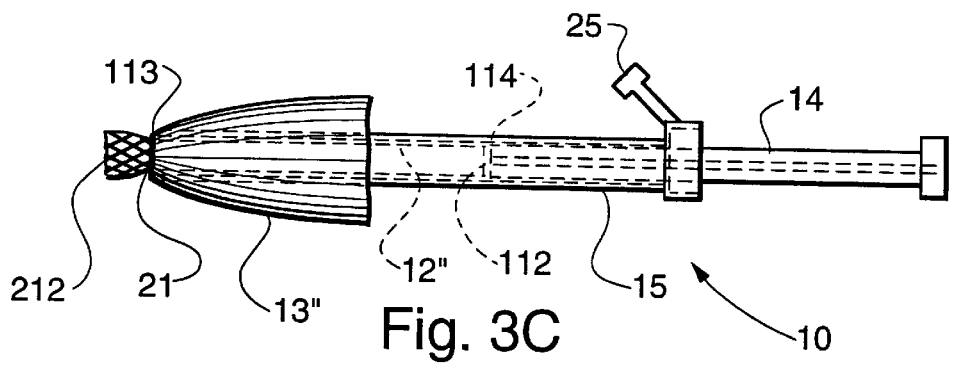
FIG. 3C is a schematic illustration of a side view of the interior sheath of FIG. 3B, showing the graft and stent linked at their respective distal ends.
Figure 3D:
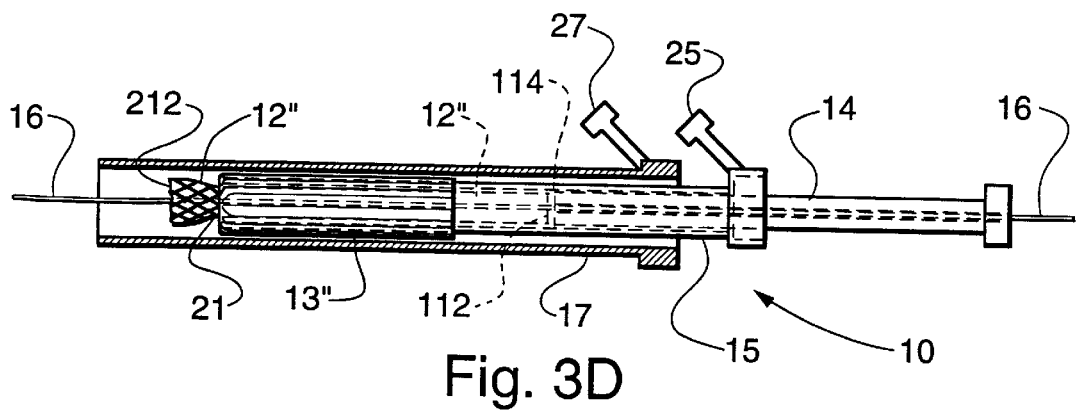
FIG. 3D is a schematic illustration of a side view of the interior sheath, stent, and graft of FIG. 3C inside the exterior sheath.
Figure 4A:
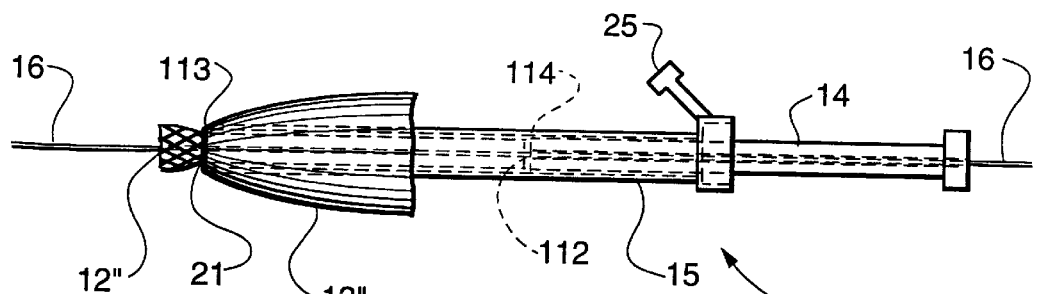
FIG. 4A is a schematic illustration of a side view of the interior sheath and attached components of FIG. 3B mounted on a guide wire.
Figure 4B:
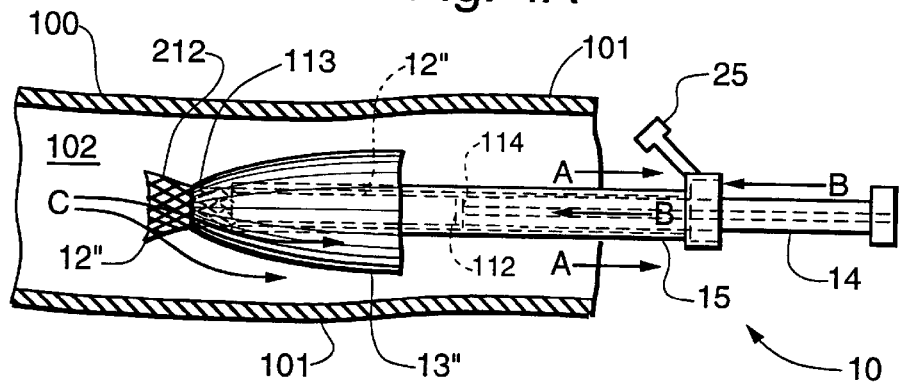
FIG. 4B is a schematic illustration of a side view of the introducer of FIG. 4A within a longitudinal section of a body lumen.
Figure 4C:
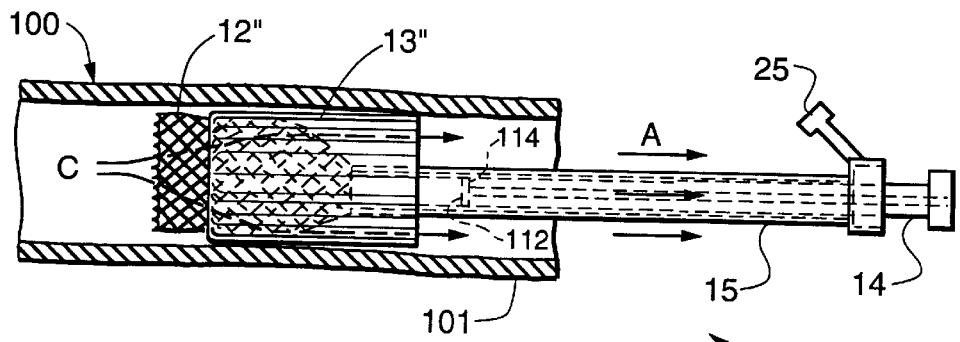
FIG. 4C is a schematic illustration of a side view of the introducer of FIG. 4B showing partial deployment of the stent and graft.
Figure 4D:
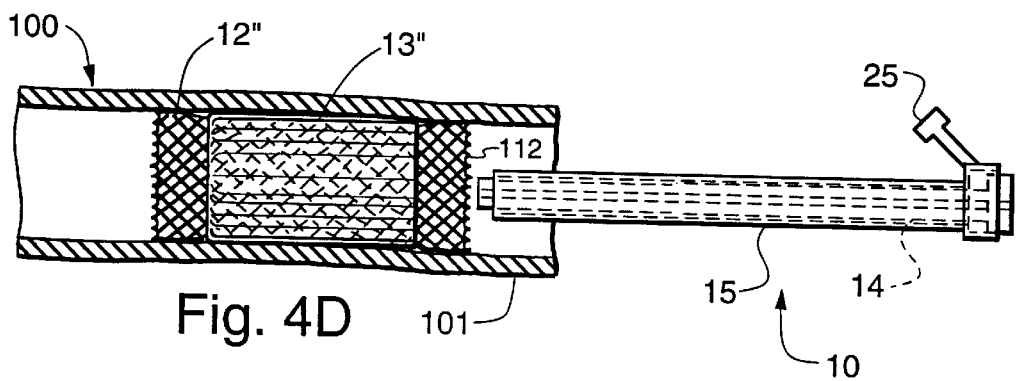
FIG. 4D is a schematic illustration of a side view of the introducer of FIG. 4C showing completed deployment of the stent and graft with interior sheath fully retracted.

Referring now to the drawing, wherein like reference numerals refer to like elements throughout, FIGS. 3A–4D show an exemplary introducer 10 for placing an endovascular stent 12" concurrently with an endovascular graft 13". Introducer 10 may be endoluminally inserted inside vascular duct 100, as shown in FIGS. 4B–4D, by means of a guide wire 16, as shown in FIGS. 3D and 4A. As shown in FIG. 3D, introducer 10 comprises an introducer exterior sheath 17 inside of which an interior sheath 15 is placed, inside of which stent 12" is compressed. Pusher 14 is positioned at proximal end 112 of stent 12". Stent distal end 212 projects from interior sheath 15 and is connected to distal end 113 of graft 13" by link 21. As used herein and consistent with commonly used terminology, the term "proximal" means closer to the access location to the body lumen outside the body, and the term "distal" means further from such access location. The portion of graft 13" proximal link 21 is secured between sheaths 15 and 17. Sheaths 15 and 17 may have respective valvular means 25 and 27.

Figure 1:
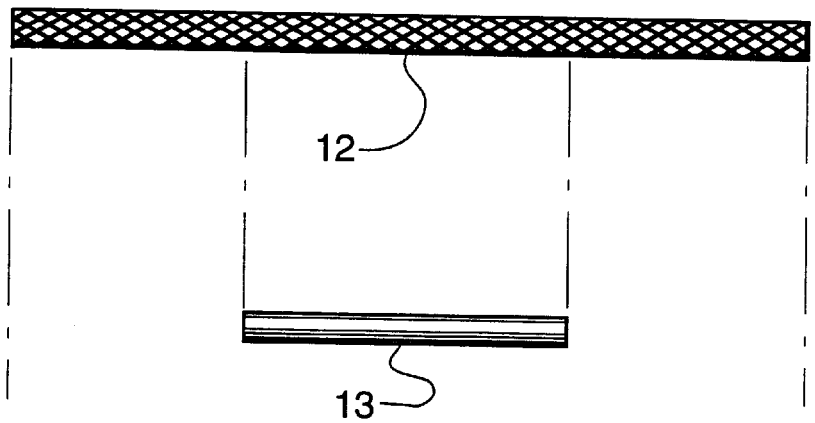
FIG. 1 is a schematic illustration of a side view of an exemplary stent and graft in their respective radially-expanded positions.

Graft 13" is typically tubular with flexible walls, and is inserted into introducer 10 in a shrunken state similar to that of graft 13' as shown in FIG. 1. Stent 12" is placed inside sheath 15 aligned with graft 13" on the outside of the sheath, with stent distal end 212 having a link 21 to the corresponding graft distal end 113, as shown in FIGS. 3C–4C.

Stent 12" is placed so that it is compressed within interior sheath 15. Proximal end 112 of stent 12" is adjacent to pusher 14, as shown in FIGS. 3B–4C. Pusher 14 has a distal end 114 that is provided with a radiopaque marker.

Distal end 212 of stent 12" projects through distal end 115 of interior sheath 15. In that exterior projection, link 21 on distal end 212 of stent 12" is attached to corresponding distal end 113 of graft 13", as shown in FIGS. 3C–4B.

Graft 13" is partially expanded from the completely compressed state of graft 13 as shown in FIG. 1, so that the graft covers distal end 115 of interior sheath 15, in which the compressed stent 12" is placed, as shown in FIG. 3C.

The components of introducer 10 as shown in FIG. 3C are placed inside exterior sheath 17 which covers graft 13", such that the graft is placed between the exterior sheath 17 and the interior sheath 15, as shown in FIG. 3D.

Figure 2:
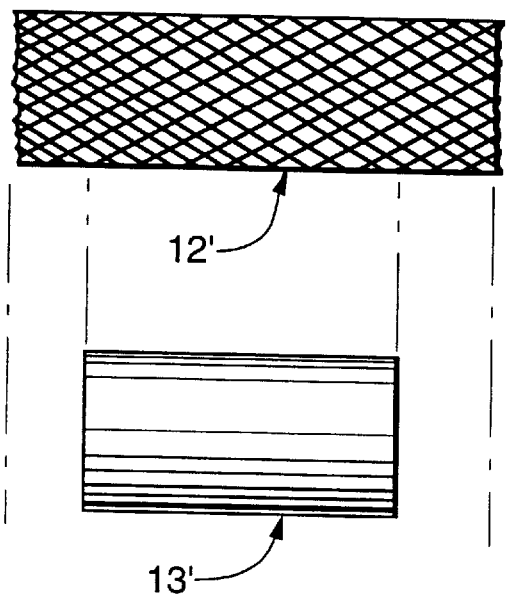
FIG. 2 is a schematic illustration of a side view of the stent and graft of FIG. 1 in their respective compressed positions.

As discussed in the background section of this application, graft 13" typically has flexible walls that expand without experiencing a significant change in length, if at all. On the other hand, when compressed stent 12 is liberated from sheath 15, the stent experiences a radial expansion together with a longitudinal reduction, as illustrated by stents 12 and 12' in FIGS. 1 and 2. Because stent 12" acts as a radial support of graft 13", the body of graft 13" has a shorter length than the length of stent 12" when it is in a radially expanded state in the desired intraluminal position, as shown in FIG. 4D.

To concurrently place stent 12" and graft 13" using introducer 10, a guide wire 16 is put into position in vascular duct 100, as is well known in the art. Introducer 10 is then threaded along guide wire 16, as shown in FIG. 4A until it reaches a desired position. Once at this position, exterior sheath 17 is retracted in the direction of arrows A while the pusher advances relative to the sheath in the direction of arrows B, leaving the partially compressed graft 13" exposed inside vascular duct 100 in a desired location, as shown in FIG. 4B.

Interior sheath 15 is gradually removed, liberating stent 12", which expands radially. This gradual expansion causes a correlative expansion of the flexible walls of graft 13" until the graft is pressed against vascular walls 101 by stent 12". At the same time, a radiopaque substance at distal end 114 of pusher 14 allows movement of the stent 12" to be monitored and thus controlled. While the aforesaid operations are carried out, the introducer still allows the flow of blood 102 along arrows C, as shown in FIGS. 4B and 4C.

Although illustrated and described herein with reference to certain specific embodiments, the present invention is nevertheless not intended to be limited to the details shown. For example, the stent/graft combination and related methods and deployment systems described in the detailed description are not intended to be limited only to vascular deployment, but are applicable to uses in other body lumen as well, similar to other stent/graft prosthesis architectures and related systems and methods well-known in the art. In addition, various modifications may be made in the details within the scope and range of equivalents of the claims and without departing from the spirit of the invention.

What is claimed is:

1. A prosthesis adapted for deployment inside a body lumen in a distal deployment location from a proximal access location outside the body lumen, the prosthesis comprising:

a graft having flexible walls and a distal end; and an expandable stent underlying said graft and having a distal end, wherein said stent and said graft are linked together only at or near the distal end of said stent and the distal end of said graft, and said prosthesis is adapted to allow endoluminal fluid flow proximally across said stent and within the walls of said graft during deployment of said prosthesis.

2. The prosthesis of claim 1 wherein:

said stent has a first axial length in a compressed radial configuration and a second axial length in an expanded radial configuration, the first axial length of the stent exceeding the second axial length of the stent; and said graft has a first axial length in a compressed radial configuration and a second axial length in an expanded radial configuration.

3. The prosthesis of claim 2 wherein the first axial length of the graft is essentially equal to the second axial length of the graft.

4. The prosthesis of claim 2 wherein the first axial length of the graft exceeds the second axial length of the graft by a difference in graft length.

5. The prosthesis of claim 4 wherein the first axial length of the stent exceeds the second axial length of the stent by a difference in stent length and the difference in stent length exceeds the difference in graft length.

6. The prosthesis of claim 2 wherein the second axial length of the stent is greater than the second axial length of the graft.

7. The prosthesis of claim 1 wherein the graft distal end is attached near the stent distal end at a location proximally spaced from the stent distal end.

8. The prosthesis of claim 1 wherein the stent comprises a thermosensitive self-expanding stent or a stent that is self-expanding through structural elasticity.

9. The prosthesis of claim 1 wherein said graft and said stent are linked together at a single axial location.

10. The prosthesis of claim 1 wherein the stent underlies the graft approximately co-extensively with the graft.

11. The prosthesis of claim 1 wherein the stent comprises a solitary stent.

12. A prosthesis adapted for deployment inside a body lumen in a distal deployment location from a proximal access location outside the body lumen, the prosthesis comprising:

a graft having flexible walls, a distal end, a first axial length in a compressed radial configuration, and a second axial length in an expanded radial configuration;

an expandable stent underlying said graft and having a proximal end, a distal end, a first axial length in a compressed radial configuration, and a second axial length in an expanded radial configuration, the first axial length of the stent exceeding the second axial length;

wherein said stent and said graft are linked together only at or near the distal ends thereof.

13. A prosthesis adapted for deployment inside a body lumen in a distal deployment location from a proximal access location outside the body lumen, the prosthesis consisting of:

a graft having flexible walls and a distal end;

an expandable stent underlying said graft and having a distal end, and a link at or near the distal end of said stent and the distal end of said graft for linking said stent and said graft together.

* * * * *